(12) United States Patent
Sullivan et al.

(10) Patent No.: US 6,402,965 B1
(45) Date of Patent: Jun. 11, 2002

(54) SHIP BALLAST WATER ULTRASONIC TREATMENT

(75) Inventors: Patrick K. Sullivan; Robert E. Bourke, both of Honolulu, HI (US); Christopher J. Sullivan, Milwaukee, WI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 13 days.

(21) Appl. No.: 09/615,709

(22) Filed: Jul. 13, 2000

Related U.S. Application Data
(60) Provisional application No. 60/143,524, filed on Jul. 13, 1999.

(51) Int. Cl.[7] .................................................. C02F 1/36
(52) U.S. Cl. ...................... 210/748; 210/136; 210/416.1
(58) Field of Search .................................. 210/748, 747, 210/170, 232, 241, 416.1, 136; 422/20

(56) References Cited

U.S. PATENT DOCUMENTS

| | | | | |
|---|---|---|---|---|
| 2,585,103 | A | * | 2/1952 | Fitzgerald |
| 4,032,438 | A | * | 6/1977 | Koblanski |
| 4,308,006 | A | * | 12/1981 | Koblanski |
| 5,164,094 | A | * | 11/1992 | Stuckart |
| 5,368,748 | A | * | 11/1994 | Sanderson |
| 5,395,592 | A | * | 3/1995 | Bolleman et al. |
| 5,441,179 | A | * | 8/1995 | Marsh |
| 5,611,993 | A | * | 3/1997 | Babaev |
| 5,711,888 | A | * | 1/1998 | Trampler et al. |
| 6,071,473 | A | * | 6/2000 | Darwin |

FOREIGN PATENT DOCUMENTS

CA 2151874 * 12/1996

* cited by examiner

Primary Examiner—David A. Simmons
Assistant Examiner—Fred Prince
(74) Attorney, Agent, or Firm—James Creighton Wray; Meera P. Narasimhan

(57) ABSTRACT

Ballast water is treated by applying ultrasonic frequencies to the water to kill organisms entrained in the water such as diatoms, veligers, fish larvae, plankton, and microorganisms, preventing the introduction of non-indigenous species between ports-of-call. The ballast water is circulated through a ballast treatment system. A pump is connected to a tube lined with a piezoelectric material for aiding in transmitting the ultrasonic frequencies connected to one or more ballast tanks of a ship. The use of the piezoelectric material as a lining allows a broad range of sound wavelengths and energy levels to be transmitted greater distances before problems with uniform sound penetration and energy loss within the sound field occur. Additionally, spatially-controllable, continuous constructive interference zones may be generated within the piezoelectric-lined tubes to specifically target the particular organisms entrained within the ballast water being treated. The treatment system includes a transducer pipe connected to diffusers and shrouds. The diffusers are closed at ends not connected to the pipe. The treatment system is provided in the ballast intake/drain device to route the ballast water through the treatment system. Ballast water is supplied through inlets in the shrouds into the diffuser which circulate the water through the tube which is lined with piezoelectric transducer material and then exhausted after treatment. The ultrasonic waves destroy organisms and prevent transfer of non-indigenous species between ports.

36 Claims, 4 Drawing Sheets

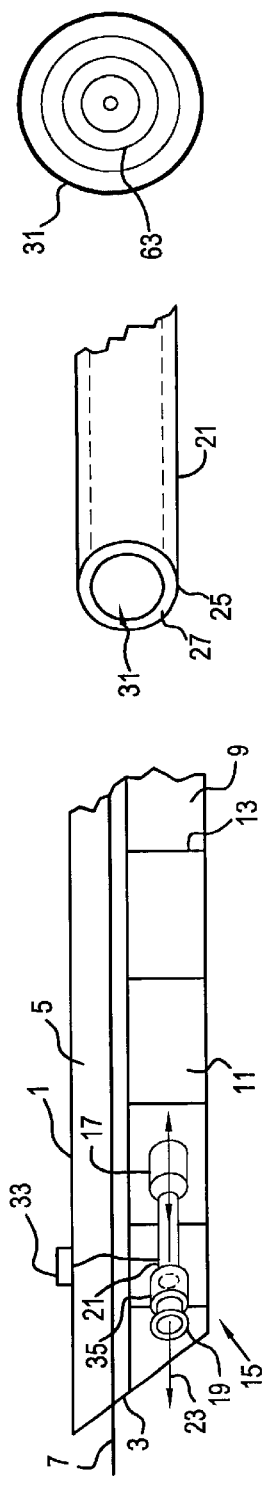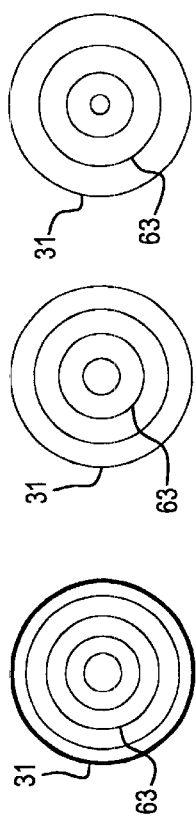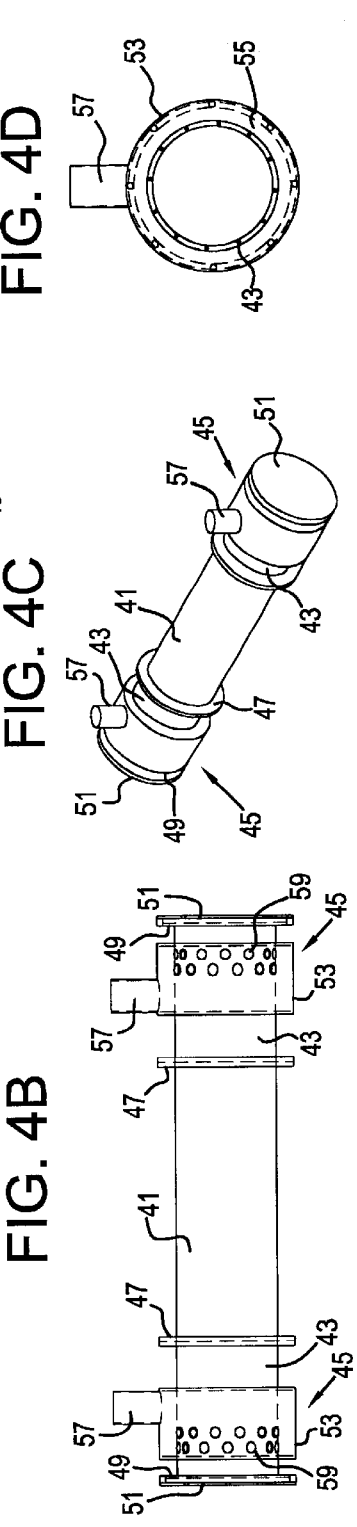

FIG. 5
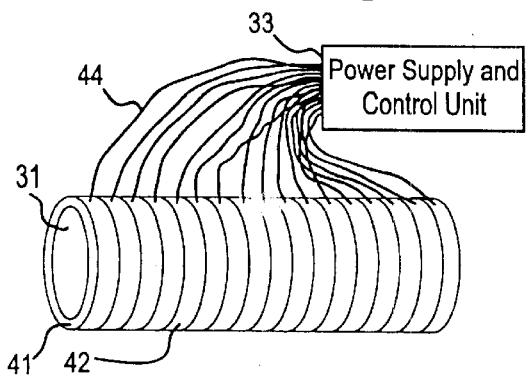
FIG. 6
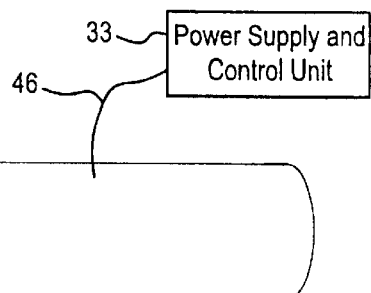
FIG. 7
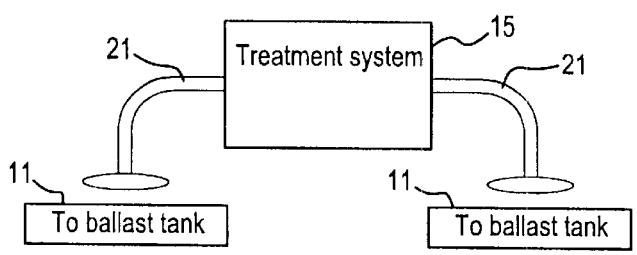
FIG. 8A
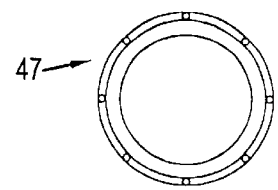
FIG. 8B   FIG. 8C   FIG. 8D   FIG. 9A
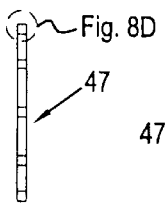 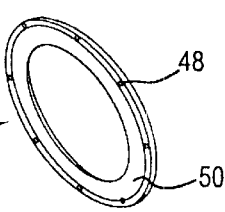 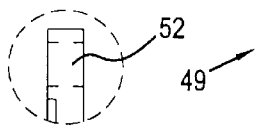 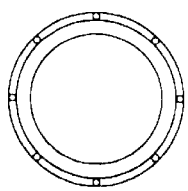
FIG. 9B   FIG. 9C   FIG. 9D   FIG. 10A
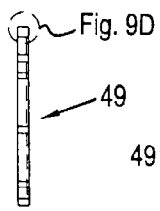 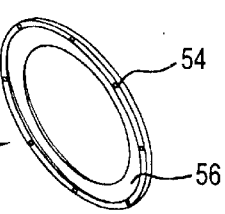 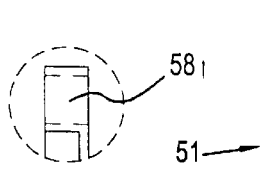 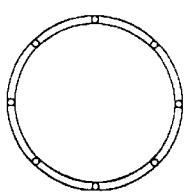
FIG. 10B   FIG. 10C   FIG. 10D
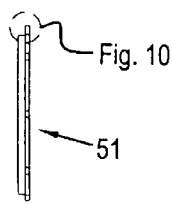 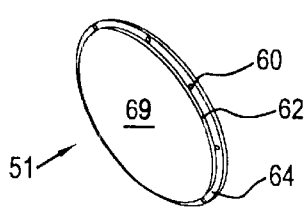 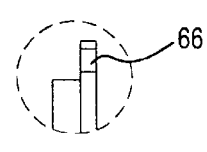

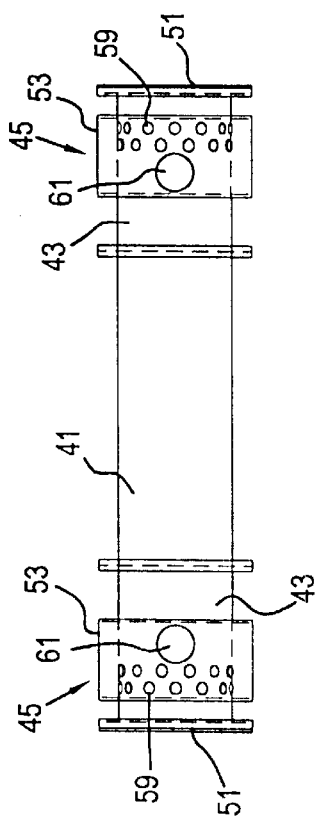
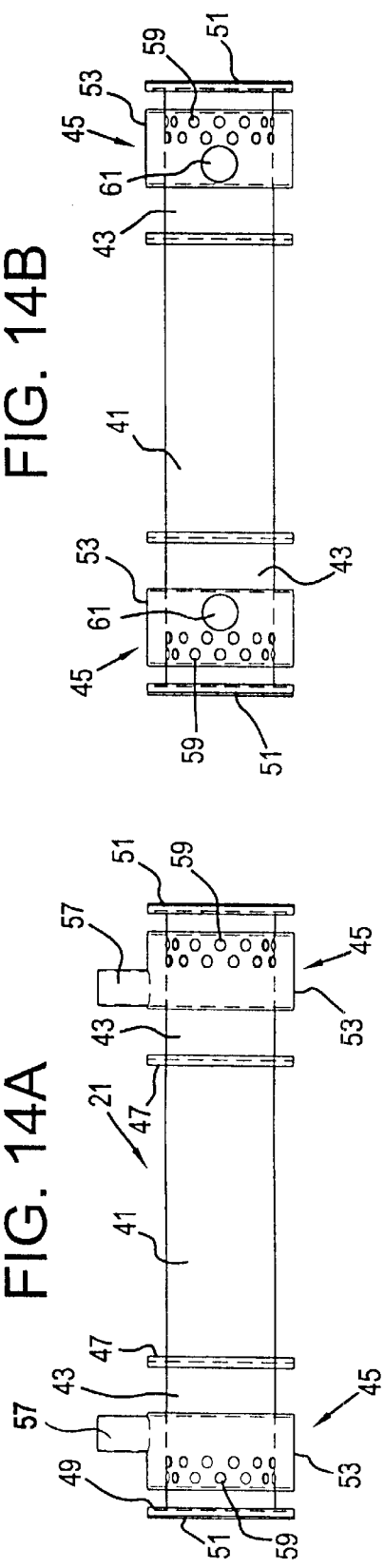
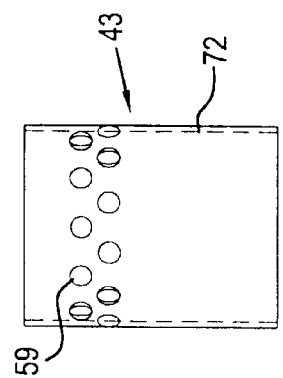
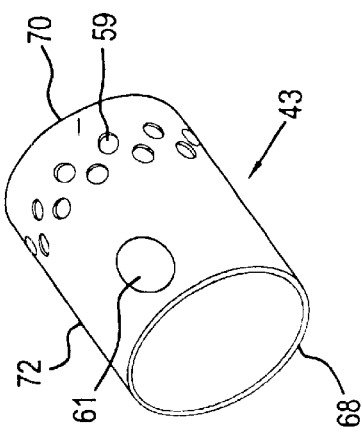

SHIP BALLAST WATER ULTRASONIC TREATMENT

This application claims the benefit of U.S. Provisional Application No. 60/143,524, filed Jul. 13, 1999.

BACKGROUND OF THE INVENTION

The transportation and introduction of non-indigenous species in ship ballast water has created substantial economic and environmental impact throughout the world. Ballast water transport of alien species has been determined to be a national environmental preservation issue of the highest priority. Zebra mussels in the Great Lakes, toxic dinoflagellates in Australia, stinging jellyfish along the California coast, and numerous fish and invertebrate species in Hawaii have all been transported into new predator-free habitats via ship ballast water. These introductions have caused broad environmental impact, have cost millions of dollars in remedial actions, and have focused government regulators on the development of controls that will have serious ramifications to both commercial and military shipping.

To address this problem, the United States Congress passed the Non-indigenous Aquatic Nuisance Prevention and Control Act of 1990, and further directed the National Research Council to prepare a report on the problem. That report, Stemming the Tide (Natl. Acad. Sci., 1996), lists several potential control mechanisms and discusses the merits and shortcomings of each. For example, while filtration of the ballast water may seem to be a logical solution, the volume and rate of filtration (to 25,000 m$^3$/hr), coupled with occasional heavy silt loads, make this option unacceptable. Other methods, including the use of biocides, ozonation, ultraviolet treatment, deoxygenation, magnetic fields and sonication, have been tested, each with operational or economic shortcomings.

Tests involving sonication were effective at killing the veliger (larval) stage of the zebra mussel under well-defined conditions. Ultrasonics have been shown to be effective in destroying micro-organisms, including bacteria and fungi, at various frequencies and intensities. High intensity sound bursts created by underwater electrical arcs have been shown to be effective against some fouling problems encountered in electrical plant cooling water intake systems. However, problems with uniform sound wave penetration and energy loss at various points within the sound field limit the use of these techniques. These problems are largely a function of the method of sound production from a limited number of transducers and sound energy attenuation away from the nodes.

Needs exist for control of unwanted biological material in transportation and relocation of large water volumes.

SUMMARY OF THE INVENTION

The invention solves the problem by providing a new ship ultrasonic ballast water treatment system to eliminate the transfer of non-indigenous marine species between ports of call.

The invention provides a new concept in underwater sound generation that effectively eliminates problems of sound energy attenuation and "blind" spots within the sound field. A continuous piezoelectric transducer, either polyvinylidene fluoride or piezoceramic, is used to generate a broad range of sound wavelengths and energy levels within a pipe. Further, use of this technology provides an ultrasonic system with great potential. Importantly, the correct geometric configuration produces spatially-controllable, continuous, constructive-interference zones to enhance the destructive force generated in the pipe lumen, and to provide the complete destruction of micro-organisms, algae, diatoms, veligers and fish larvae and other plankton.

The insides of the in-take and out-take manifolds are sheathed with the piezoelectric material to create one long, continuous sound transducer tube within the pipe. This presents a complex array of high intensity sound through which all of the ballast water and entrained organisms enter or leave the ship.

When ballast water management is required aboard ships, the use of sonification to effectively sterilize ballast water is relatively easily implemented without costly shoreside facilities, nor does it require mid-ocean ballast water changes.

This same technique also provides a method to keep seawater coolant intakes on shore-based power-generation facilities, and those on board surface vessels or submarines, free of fouling organisms without the use of caustic or otherwise hazardous chemicals.

Ultrasonic ballast water treatment systems have shown variable results due to design and construction limitations. For conventional configurations, the intensity varies as a function of the distance from the source, limiting the effectiveness of the device. The use of a piezoelectric material to line a cylindrical tube offsets the problems of varied spatial intensity in discrete transducer systems and provides a continuous source of axi-symmetric ultrasonic excitation. Constructive interference, controlled by design geometry and modulation of the ultrasound frequency input, can be produced in a spatially-sweeping manner to further enhance the pressure fluctuation amplitude. Additionally, design geometry may be varied by linear section to enhance section resonance characteristics. Application of a transducer to the end of a diffuser pipe is also used to create uniform spatial intensity.

A preferred embodiment of a ballast intake and exhaust tube comprises a section of middle pipe and a diffuser pipe and a shroud connected to each end of the middle pipe. The shroud houses the end of the diffuser pipe. In a preferred embodiment, the middle pipe is connected to the diffuser pipe by quarter-inch flanges and half-inch flanges. The diffuser pipe is terminated by an end plate. This end plate stops the flow of ballast water, and allows the water to be circulated back through the piezoelectric transducer, which lines the middle and diffuser pipe, or is mounted at the end of the diffuser.

Preferably, the shroud housing the diffuser pipe comprises a cylindrical tube into which are fitted two or more seating rings. The seating rings hold the diffuser pipe in place within the shroud. Additionally, a cylindrical extension extends from the cylindrical tube of the shroud.

A preferred embodiment of a diffuser pipe comprises a section of pipe having the same diameter as the middle pipe with holes cut into one end. Additionally, a larger hole is cut into the diffuser pipe to align with the cylindrical extension of the shroud into which the diffuser pipe is placed. In a preferred embodiment, the end of the diffuser pipe into which holes are cut is terminated by an end plate.

This invention allows for uniform and controllable sound fields and symmetric interference patterns throughout the entire pipe volume.

These and further and other objects and features of the invention are apparent in the disclosure, which includes the above and ongoing written specification, with the claims and the drawings.

BRIEF DESCRIPTION OF THE DRAWINGS

FIG. 1 is a schematic representation of a ship hull with a ballast tank and an intake and exhaust tube.

FIG. 2 is a schematic representation of an intake and exhaust tube.

FIGS. 3A–3D are front elevation views of a piezoelectric transducer differently resonating ultrasonic frequencies.

FIG. 4A is a top elevation view of a ballast intake and exhaust tube.

FIG. 4B is a side elevation view of a ballast intake and exhaust tube.

FIG. 4C is a perspective view of a ballast intake and exhaust tube.

FIG. 4D is a front elevation view of a ballast intake and exhaust tube.

FIG. 5 is a perspective view of linked power supply and control units connecting a plurality of portions forming the tube.

FIG. 6 is a perspective view of a power supply and control unit.

FIG. 7 is a schematic representation of a ballast water treatment system.

FIG. 8A is a top view of a flange.

FIG. 8B is a side elevation view of the flange.

FIG. 8C is a bottom perspective view of the flange.

FIG. 8D is an enlarged close-up of a flange end of FIG. 8B.

FIG. 9A is a is a top view of another flange.

FIG. 9B is a side elevation view of the flange.

FIG. 9C is a bottom perspective view of a flange.

FIG. 9D is an enlarged close-up of a flange end of Figure 9B.

FIG. 10A is a top elevation view of an end plate.

FIG. 10B is a side elevation view of an end plate.

FIG. 10C is a perspective view of an end plate.

FIG. 10D is an enlarged close-up of a flange end of FIG. 10B.

FIG. 14A is a side elevation view of a ballast intake and exhaust tube.

FIG. 14B is a top elevation view of a ballast intake and exhaust tube.

FIG. 15A is a perspective view of a diffuser.

FIG. 15B is a side elevation view of a diffuser.

FIG. 15C is an end elevation view of a diffuser.

DETAILED DESCRIPTION OF THE PREFERRED EMBODIMENTS

Figure 11A:
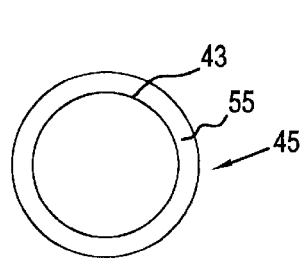
FIG. 11A is a front elevation view of a seating ring for positioning a diffuser pipe within a shroud.
Figure 11B:
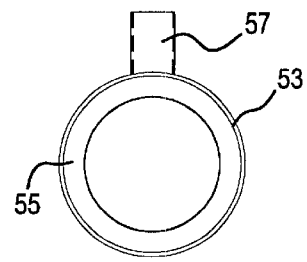
FIG. 11B is a front elevation view of a shroud.
Figure 11C:
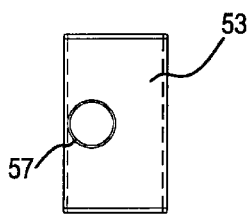
FIG. 11C is a top elevation view of the shroud.
Figure 11D:
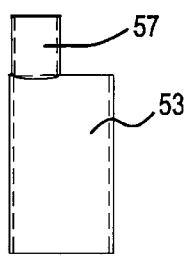
FIG. 11D is a side elevation view of the shroud.
Figure 11E:
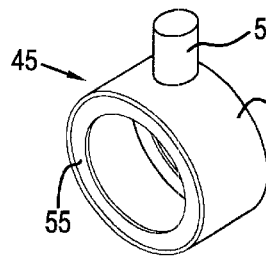
FIG. 11E is a perspective view of the shroud.
Figure 12A:
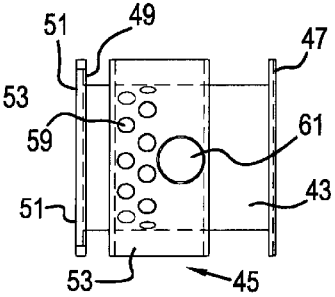
FIG. 12A is a top elevation view of a diffuser.
Figure 12B:
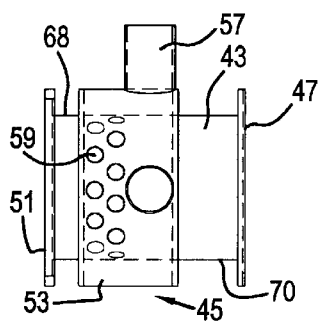
FIG. 12B is a side elevation view of the diffuser.
Figure 12C:
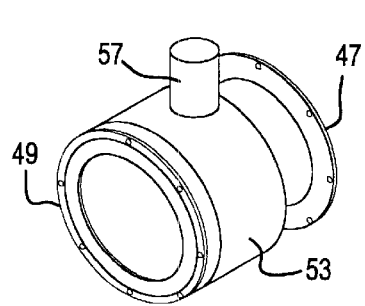
FIG. 12C is a perspective view of the diffuser within the shroud.
Figure 12D:
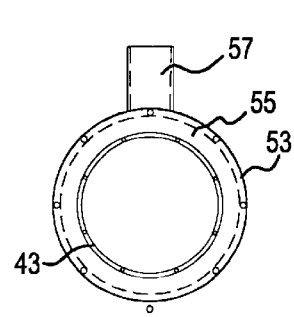
FIG. 12D is a front elevation view of the diffuser pipe within the shroud.

Referring to FIG. 1, a ship hull is generally indicated by the numeral 1. The ship has a bow 3 and a stern, which is not shown, and a freeboard area 5 above a waterline 7. The bulk 9 of the ship is below the waterline. The ship has one or more ballast tanks 11 with internal partitions 13.

A reversible ballast intake and exhaust system 15 has a reversible ballast pump 17 and a sea valve 19 at opposite ends of a ballast treatment tube 21. Exhausting 23 ballast water into a port while taking on cargo or taking in ballast water from the body of water within the port transfers unwanted biological material, for example in the form of small marine animals, plankton, plant materials, bacteria and viruses. As shown schematically in FIG. 7, the ballast water ultrasonic treatment system 15 connects to the ship ballast tanks 11 via the ballast treatment tubes 21.

A ship in ballast is substantially empty of cargo, and its only cargo is the water which it carries from one port to another port. Discharging that water from the cargo offloading port to the cargo onloading port, for example while taking on grain in the Great Lakes, in large volumes may alter the marine ecology of the port. While most of the biological material transferred with the ballast water is innocuous, some noxious and unwanted materials may be transported and transferred.

To guard against such transportation and release of unwanted biological materials, the present invention provides a new ballast intake and exhaust tube 21 shown in FIG. 2. Tube 21 has a tubular support structure 25, such as steel, and an internal liner 27, which is a continuous piezoelectric transducer 31. The piezoelectric transducer 31 is operated by a shipboard power supply and controller 33, shown in FIGS. 5 and 6, which is computer controlled to generate a broad range of sound wavelengths and energy levels within the pipe 21

The transducer 31 provides the correct geometric configuration to produce spatially controlled continuous constructive interference zones to enhance the destructive force of the sonic waves within the pipe to provide the complete destruction of micro-organisms, algae, diatoms, veligers, larvae and plankton.

As seen in FIGS. 1-2, the tube 21 may comprise a series of intake tubes in a manifold, each of the tubes in the manifold being lined with the continuous piezoelectric transducer 31. Each tube 21 may be provided with a check valve 35 so that the pump 17 may be continuously operated during the voyage with the sea valve 19 closed so that ballast water is continuously circulated through the transducer 31 while the ship is underway, anchored or lying to. Once the appropriate amount of ballast has been taken in, the sea valve 19 is closed and the pump is reversed to exhaust ballast through check valve 35 back into the tank 11, for continuously recirculating ballast from the ballast tank 11 through the piezoelectric transducer 31 within tube 21 for complete destruction of all biological materials. All of the ballast water passing into or out of the ballast tanks 11 is pumped 17 through the continuous transducer 31 within the tube 21.

FIGS. 3A–3D each show a piezoelectric transducer 31 resonating ultrasonic frequencies 63 in differing patterns of resonating sonic waves. Preferably the continuous piezoelectric transducer 31 is made of, but not limited to, polyvinyliderie fluoride or piezoceramic material.

FIG. 4A–4D show a preferred embodiment of the tube 21. Tube 21 comprises one or more pipes 41, with diffusers 43 and shrouds 45 on ends of pipes 41. Shroud 45 houses ends of the diffuser 43. Preferably, pipes 41 are connected to the diffusers 43 by flanges 47 which may be of differing sizes such as, but not limited to, quarter-inch or half inch flanges. End-plates 51 positioned on flanges 49 at ends of the tube 21 close off ends of the diffusers 43. A transducer is substituted for End-plates 51 for longitudinal sonification. Extensions or lines 57 are inlets/outlets for supplying and exhausting ballast water into and from the pipe 41 respectively. Openings 59 are provided on diffusers 43 for receiving the water from the shroud 45 and circulating in the transducer tube 21. Larger openings 61 on diffusers 43 are aligned with the lines or extensions 57 of the shrouds 45.

As seen in FIGS. 5 and 6 the pipe 41 may either be one elongated pipe (FIG. 6) or be made of a plurality of sections 42 (FIG. 5). Plural power cords 44 connect each of the plural sections 42 to the power supply and control unit 33. Cord 46 connects the elongate pipe 41 to the control unit 33. control unit 33 may be manually or remotely operated or may have sensors to trigger ultrasonication of ballast water as and when treatment is necessary.

FIG. 7 shows a schematic of the treatment system in which water from ballasts 11 are subjected to the inventive treatment system 15 along intake/exhaust tube 21 to remove undesirable organisms from the ballast water.

FIGS. 8A–8D show details of flanges 47 that connect pipe 41 and diffusers 43. Flanges 47 on ends of pipe 41 are substantially planer and have openings 48 for connecting with similar flanges 47 on ends of diffusers 43. Flanges 47 are ring-like and enable a tight-fit between the pipe 41 and diffusers 43. Gaskets 50 may be provided in grooves 52 for leak proof fitting.

FIGS. 9A–9D show flanges 49 that connect the diffuser ends and end plates. Flanges 49 may be ring-like and have openings 54 for receiving fasteners to connect to complementary openings in end plates. Gaskets 56 in grooves 58 enable a leak proof fitting.

End plate 51 shown in FIGS. 10A–10C prevent the escape of ballast water supplied to the transducer 31 within pipe 41 and force the circulation of ballast water through the piezoelectric transducer 31 (FIGS. 4A–4D). End plate 51 may have a plate-like planar structure 66 surrounded by ring-like edge flange 62 having openings 60 complementary to openings 54 in flanges 49 for receiving fasteners and connecting with flanges 49 on ends of diffusers 43. Gaskets 64 may be provided in grooves 66 for tight-fitting of the end plates with the diffusers.

Shrouds 45 house the diffusers 43. Shown in FIG. 11A, the seating rings 55 hold the diffusers 43 in place within the shrouds 45. FIGS. 11B–E show a preferred embodiment of a shroud 45. Preferably, the shroud 45 comprises a cylindrical tube 53 having one or more seating rings 55. Lines 57 are connected to the hollow shroud 45. Lines 57 may be inlets and outlets that may be used interchangeably for supplying and exhausting ballast water into and out of the shroud, the diffusers 43 and the pipe 41 (FIG. 4A).

FIGS. 12A–D show a diffuser pipe 43 fitted in a shroud 45. Cylindrical extension or line 57 extends from the cylindrical tube 53 of the shroud 45. Line 57 may be an inlet or outlet for supplying and exhausting ballast water into diffuser 43 and pipe 41. Ends 68 of diffuser 43 away from pipe 41 are fitted with flange 49 and end-plate 51. Ends 70 have flanges 47 for fitting on flanges 47 on pipe 41.

Figure 13A:
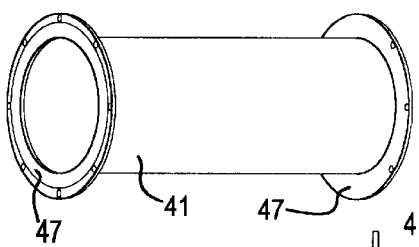
FIG. 13A is a side elevation view of a pipe.
Figure 13C:
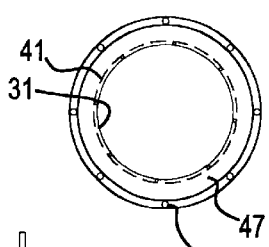
FIG. 13C shows a side elevation of the pipe and flange.
Figure 13B:
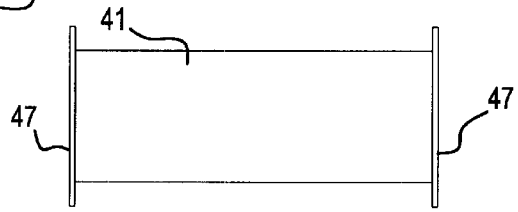
FIG. 13B is a perspective view of the pipe.

FIGS. 13A–13C show the pipe 41 having end flanges 47 and housing piezoelectric transducer 31. Flanges 47 have openings 48 complementary to openings in flanges 47 on diffusers 43 for connecting the diffusers and the pipe 41.

FIGS. 14A and 14B show an assembled preferred embodiment of a ballast water intake and exhaust tube 21. The tube 21 comprises one or more sections of middle pipe 41, with a diffuser 43 and a shroud 45 on each end of the middle pipe 41. The shroud 45 houses the ends of the pipe 43. In a preferred embodiment, the pipe 41 is connected to the diffusers 43 by flanges 47.

A preferred embodiment of a diffuser 43 is shown in FIGS. 15A–15C. The diffuser 43 comprises a section of pipe 72 preferably of the same diameter as the middle pipe 41 with cut-outs or openings 59 along a circumference of the diffuser, preferably towards an end of the diffuser. Additionally, larger openings 61 in the diffuser align with the lines or extensions 57 of the shroud 45 into which the diffuser pipe 43 is placed. In a preferred embodiment, one end 68 of the diffuser 43 is connected to the pipe 41 by flanges 47 and the other end 70 of the diffuser proximal the holes or openings 59 is connected to flanges 49 and end plate 51 for closing off the diffuser end (FIGS. 4A–4D).

The insides of the in-take and out-take manifolds are sheathed with the piezoelectric material to create one long, continuous sound transducer tube 21 within the pipe. This presents a complex array of high intensity sound through which all of the ballast water and entrained organisms enter or leave the ship.

In operation, when ballast water management is required aboard ships, the use of sonification to effectively sterilize ballast water is relatively easily implemented without costly shoreside facilities, nor does it require mid-ocean ballast water changes. This same technique also provides a method to keep seawater coolant intakes on shore-based power-generation facilities, and those on board surface vessels or submarines, free of fouling organisms without the use of caustic or otherwise hazardous chemicals. The use of a piezoelectric material to line a cylindrical tube or end plate offsets the problems of varied spatial intensity in discrete transducer systems and provides a continuous source of axi-symmetric ultrasonic excitation.

Constructive interference, controlled by design geometry and modulation of the ultrasound frequency input, can be produced in a spatially-sweeping manner to further enhance the pressure fluctuation amplitude. Additionally, design geometry may be varied by linear section to enhance section resonance characteristics.

While the invention has been described with reference to specific embodiments, modifications and variations of the invention may be constructed without departing from the scope of the invention, which is defined in the following claims.

We claim:

1. A method of treating ballast water comprising providing a treatment system having a piezoelectric transducer intake/exhaust tube, controlling the transducer through a control system connected to the tube, providing the treatment system in a ballast intake/drain, transmitting ultrasonic waves through ballast water passing through the piezoelectric transducer tube and treating the ballast water.

2. The method of claim 1, wherein the treating comprises destroying organisms in ballast water by supplying the water through the tube while transmitting the ultrasonic waves.

3. The method of claim 2, wherein the organisms are selected from the group consisting of algae, diatoms, veligers, fish larvae, plankton, microorganisms, and combinations thereof.

4. The method of claim 1, wherein the transmitting comprises transmitting sound wavelengths and energy levels.

5. The method of claim 4, wherein the transmitting comprises producing continuous axi-symmetric ultrasonic excitation.

6. The method of claim 1, wherein the transmitting comprises producing constructive interference in a spatially sweeping manner.

7. The method of claim 1, wherein the treating comprises recirculating ballast water through the piezoelectric transducer.

8. An apparatus for treating ballast water comprising a ballast inlet/drain device, a ballast intake/exhaust tube connected to the device, piezoelectric material lining the tube forming a piezoelectric transducer, a control system connected to the tube for activating the transducer by supplying ultrasonic waves to the transducer, at least one inlet connected to the tube for receiving ballast water from the ballast and at least one exhaust connected to the tube for exhausting treated ballast water free of organisms.

9. The apparatus of claim 8, wherein the piezoelectric material is polyvinylidene fluoride.

10. The apparatus of claim 8, wherein the piezoelectric material is piezoceramic.

11. The apparatus of claim 8, wherein the tube has one or more linear sections.

12. The apparatus of claim 8, wherein the tube comprises a series of intake tubes lined with piezoelectric material within a manifold.

13. The apparatus of claim 12, wherein each intake tube further comprises a check valve.

14. The apparatus of claim 12, wherein the piezoelectric material is selected from the group consisting of polyvinylidene fluoride and piezoceramic material.

15. The apparatus of claim 8, further comprising a tubular support structure.

16. The apparatus of claim 15, wherein the tubular support structure is steel.

17. The apparatus of claim 8, wherein the control system further comprises a power supply and a controller connected to the tube.

18. The apparatus of claim 17, wherein the power supply and control has controls for manual or computer activation.

19. An apparatus for treating ballast water comprising a reversible ballast pump for circulating ballast water, a treatment tube connected to the pump, piezoelectric material lining the tube for enhancing transmission of ultrasonic waves for treating and destroying organisms in ballast water.

20. The apparatus of claim 19, wherein the treatment tube comprises at least one pipe, at least one diffuser connected to the at least one pipe and at least one shroud connected to the at least one diffuser.

21. The apparatus of claim 20, wherein the at least one pipe comprises first and second ends, wherein an end is connected to the at least one diffuser.

22. The apparatus of claim 21, wherein the at least one diffuser comprises plural diffusers, and wherein the first and second ends of the pipe are each connected to a diffuser.

23. The apparatus of claim 22, wherein the at least one shroud comprises plural shrouds, and wherein each shroud is connected to a diffuser.

24. The apparatus of claim 23, wherein each diffuser has a body having opposite ends, one end being connected to one of the ends of the at least one pipe, plural openings on the body along an end, and further comprising one opening on an end opposite to that having the plural openings.

25. The apparatus of claim 24, wherein each shroud has a body with opposite ends, each end having a seating ring for receiving and positioning the diffuser.

26. The apparatus of claim 25, further comprising an extension on the shroud forming interchangeably an inlet or an outlet, wherein the one opening on the diffuser is complementary with the extension for receiving and supplying ballast water to the pipe.

27. The apparatus of claim 20, further comprising a first flange on an end of the pipe, and a complementary flange on the diffuser, the flanges having complementary openings for receiving fasteners and connecting the diffuser and the pipe.

28. The apparatus of claim 20, further comprising an end flange with openings on an end of the diffuser distal from and end proximal the pipe, and an end plate having complementary openings for connecting with fasteners to the end flange and sealing an end of the diffuser.

29. The apparatus of claim 20, further comprising piezoelectric lining on the pipe, the diffuser and the shroud.

30. The apparatus of claim 19, wherein the piezoelectric lining is selected from the group consisting of polyvinylidene fluoride and piezoceramic material.

31. The apparatus of claim 19, further comprising a control system connected to the tube.

32. The apparatus of claim 31, wherein the control system comprises a power supply connected to the tube, a source for supplying ultrasonic waves to the tube, an operating device for activating the control system and the treating ballast water with ultrasonic waves in the tube.

33. The apparatus of claim 32, further comprising a manual controller for triggering the operating device into operation.

34. The apparatus of claim 32, further comprising a remote control for triggering the operating device into operation.

35. The apparatus of claim 32, further comprising a computing device for monitoring the system, controlling operation of the system and for displaying information relating to the treatment.

36. The apparatus of claim 19, further comprising a valve connected to the treatment tube for controlling water intake into the ballast and water exhaustion into the sea.

* * * * *